United States Patent [19]

Abe et al.

[11] Patent Number: 4,460,566

[45] Date of Patent: Jul. 17, 1984

[54] HAIR RINSE COMPOSITION

[75] Inventors: Yoshiaki Abe, Tokyo; Rikio Tsushima, Wakayama, both of Japan

[73] Assignee: Kao Soap Co., Ltd., Tokyo, Japan

[21] Appl. No.: 341,054

[22] Filed: Jan. 20, 1982

[30] Foreign Application Priority Data

Jan. 27, 1981 [JP] Japan .................................. 56-10471

[51] Int. Cl.³ .............................................. A61K 7/06
[52] U.S. Cl. ...................................... 424/70; 424/71; 424/72; 424/359; 424/361
[58] Field of Search ...................... 424/359, 70, 71, 72

[56] References Cited

U.S. PATENT DOCUMENTS

| | | | |
|---|---|---|---|
| 3,033,755 | 5/1962 | Jacobi | 424/59 X |
| 3,904,748 | 9/1975 | Eckert et al. | 424/70 |
| 3,957,065 | 5/1976 | Busch et al. | 132/7 |
| 4,041,150 | 8/1977 | Karjala | 424/71 |
| 4,279,996 | 7/1981 | Yoshioka et al. | 435/69 |
| 4,283,386 | 8/1981 | Van Scott | 424/70 |

FOREIGN PATENT DOCUMENTS

| | | | |
|---|---|---|---|
| 2600514 | 7/1976 | Fed. Rep. of Germany | 424/71 |
| 2940220 | 4/1980 | Fed. Rep. of Germany | 424/71 |
| 22643 | 10/1907 | United Kingdom | 424/70 |
| 1111934 | 5/1968 | United Kingdom | 424/70 |
| 2061956 | 5/1981 | United Kingdom | 424/70 |

*Primary Examiner*—Dale R. Ore
*Attorney, Agent, or Firm*—Oblon, Fisher, Spivak, McClelland & Maier

[57] ABSTRACT

A hair rinse composition is described which comprises a defined amount of at least one decomposition derivative of keratin material such as animal hair, human hair, nail, feather, hoof and the like. The derivatives are, for example, salts of decomposition products obtained by oxidation of keratin material or salts of derivatives at thiol groups of decomposition products obtained by reduction of keratin material. Surface active agents other than cationic surface active agents may be further contained.

5 Claims, No Drawings

HAIR RINSE COMPOSITION

BACKGROUND OF THE INVENTION

1. Field of the Invention

This invention relates to hair rinse compositions which comprise decomposition derivatives of keratin material therein and show an excellent hair conditioning effect.

2. Description of the Prior Art

On washing of hair with shampoos mainly comprised of anionic surface active agents to remove stains from the hair, it will be found that an oil component protecting the hair surface as well as stains is removed. The removal of the oil component from the hair surface results in a loss of softness of the hair and thus the hair becomes lusterless and hard to comb, producing a tendency towards the damage of hair, split-ends or broken hairs.

In order to prevent these troubles and give a hair conditioning effect of imparting, to hair, softness, smoothness and wettness to the touch and improving combing ease, hair rinses have conventionally been used.

Known hair rinses are fundamentally comprised of quarternary ammonium salts which are a cationic surface active agent serving to impart softness and smoothness to hair, and oil components such as liquid paraffin, higher alcohols, and the like for supplementing an oil component to hair to form an oil film on the hair surface so that the hair is imparted with gloss, is reduced in damage owing to the frictional contact with brush, comb and the like, and is prevented from being split at ends or broken.

However, quaternary ammonium salts have no capability of stably emulsifying and dispersing oil components in amounts sufficient to produce such effects as mentioned above and thus hair rinses using such salts become unstable. Where nonionic surface active agents are added in order to overcome the above drawback, there has been involved a disadvantage in that the inherent rinsing effect lowers. Accordingly, there have been proposed hair rinses in which there are incorporated instead of the oil component anionic surface active agents, anionic polymer compounds, cationic polymer compounds, and hydrolysates of collagen. However, these rinses are not satisfactory yet.

SUMMARY OF THE INVENTION

It is accordingly an object of the present invention to provide hair rinse compositions which show excellent hair conditioning effects.

It is another object of the invention to provide hair rinse compositions which comprise decomposition derivatives of keratin material and thus exhibit more excellent in hair conditioning than known hair rinses.

It is a further object of the invention to provide hair rinse compositions which can impart good feeling of the hair to the touch.

According to the present invention, there is provided a hair rinse composition which comprises, in liquid medium, 0.01–10 wt% of at least one decomposition derivative of keratin material selected from the group consisting of (1) salts of decomposition products obtained by oxidation of keratin material and (2) salts of derivatives at thiol groups of decomposition products obtained by reduction of keratin material.

DETAILED DESCRIPTION AND EMBODIMENTS OF THE INVENTION

The keratin decomposition derivatives to be used in the present invention can be prepared by either of methods including a method of decomposing a keratin material by oxidation and converting the decomposition product into a salt, and a method of decomposing keratin material by reduction, chemically modifying thiol groups of the decomposition product to obtain a derivative thereof, and converting the derivative into a salt.

The starting keratin materials include, for example, animal hair, human hair, feather, nail, horn, hoof, scale and the like, among which wool, human hair and feather are preferably used. These keratin materials may be subjected to oxidation or reduction as they are but if necessary, they may be cut or reduced into pieces of a suitable size or subjected to pretreatments such as washing and defatting.

The decomposition of keratin material is conducted by any of the following methods.

(1) Oxidation Reaction

The oxidation of keratin material is feasible by any of methods known per se (N. H. Leon; Textile Progress, Vol. 7, Page 1 (1975)). Oxidizing agents are preferably of the type which may be either organic or inorganic but acte electrophilically on the disulfide bonds (S-S bonds) in the keratin structure. Examples of the oxidizing agent include organic peracids, inorganic peroxo acids or their salts, permanganic acid or its salts, chromic acid or related compounds, halogens, peroxides, oxyacid or their salts, and the like, among which peracetic acid, performic acid and perbenzoic acid are most preferable.

The oxidation reaction is conducted in liquid medium using an oxidizing agent in excess with respect to the disulfide bonds in keratin material generally in amounts of two equivalents or more, preferably 4–10 equivalents, per one disulfide bonds. The reaction is feasible under acidic or alkaline conditions and is preferably conducted under acidic and particularly weakly acidic conditions. The reaction temperature and pressure depend on the types of the oxidizing agent and keratin material used and thus are not critical. In general, the temperature is sufficiently room temperature but if necessary, heat may be applied. The pressure is sufficiently a normal pressure but the reaction may be carried out under reduced pressure or under pressure.

By this, the disulfide bond of keratin material is cleft into sulfonic acid.

(2) Reduction Reaction and Chemical Modification Reaction

Reducing agents employed for reducing keratin materials are preferably organic or inorganic reducing agents of the type which serves to cleave the disulfide bond in the keratin structure into a thiol group (-SH) and generally nucleophilically acts on the disulfide bond. Examples of the reducing agent include organic reducing agents such as mercaptoethanol, thioglycollic acid, benzylmercaptan, 1,4-dithiothreitol, tributylphosphine and the like, and inorganic reducing agents such as sodium hydrogensulfite, sulfides such as sodium hydrosulfide, metallic hydrides such as lithium aluminium hydride, and the like.

The amount of the reducing agent is usually in the range of 2–10 equivalents with respect to the disulfide bonds in keratin material. The pH of the reaction system is in the range of 2-12, preferably 6-11. Outside the range, the hydrolysis undesirably takes place at the same time. The reaction temperature is sufficiently room temperature but heat may be applied to shorten the reaction time is ordinarily in the range of 2-3 hours or more. Since the thiol groups produced by the reduction should not substantially be oxidized, so that the reduction operation should conveniently be carried out in an atmosphere of inert gas to give good results.

The decomposition product obtained by the reduction of keratin material is then chemically modified at the thiol groups thereof to obtain a derivative thereof. The derivatives at the thiol groups include:

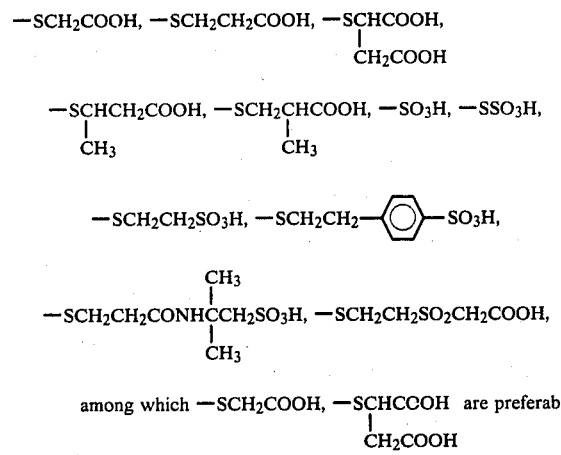

among which $-SCH_2COOH$, $-SCHCOOH$ are preferable.
$\qquad\qquad\qquad\qquad\qquad\qquad\ \ \ |$
$\qquad\qquad\qquad\qquad\qquad\qquad CH_2COOH$ The chemical modification of the thiol group can be made by any procedures known per se, for example, on the basis of procedures described in N. H. Loen; Textile Progress, Vol. 7, Page 1 (1975), "Yuuki Ioo Kagobutsu (Organic Sulfur Compounds)" written by Shigeru Ookyo and published by Kagaku Dojin (1968), and "Kobunshi Jikkengaku Koza" written by Masami Oku, Vol. 12, Kyoritsu Shuppan (1975). Typical methods are described below:

(1) Method utilizing the nucleophilic substitution reaction of SH group

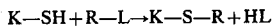

(in which K represents a residue of keratin compound, R represents a chemically modifying group to be introduced, and L represents a releasing atom or group such as a halogen atom or an acid residue).

Compounds reacting by this method include, for example, halogen compounds such as iodoacetic acid, bromoacetic acid, chloroacetic acid and the like.

(2) Method utilizing the nucleophilic addition reaction of SH group with a carbon-carbon double bond

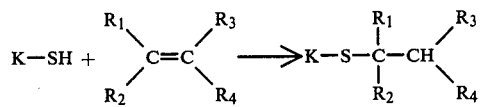

(in which at least one of $R_1$, $R_2$, $R_3$ and $R_4$ represents a carboxyl group or sulfonic acid group, the other represent an alkyl group or hydrogen atom, and K has the same meaning as defined hereinbefore).

Compounds reacting by this method include, for example, acrylic acid, methacrylic acid, crotonic acid, maleic acid, fumaric acid, vinylcarboxymethylsulfonic acid, vinylsulfonic acid, styrenesulfonic acid, 2-acrylamido-2-methylpropanesulfonic acid and the like.

(3) Method using a substitution reaction between SH group and sulfite compound

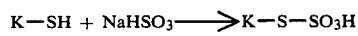

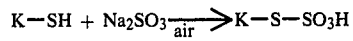

(in which K has the same meaning as defined hereinbefore).

(4) Method of oxidizing SH group into sulfonic acid group

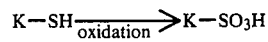

(in which K has the same meaning as defined hereinbefore). The oxidizing agents useful in this reaction include, for example, halogens, permanganates and the like.

Salts of the oxidation decomposition products and reduction derivatives of keratin material include salts of inorganic alkalis such as sodium, potassium and the like, ammonium salts, salts of organic bases such as ethanolamine, diethanolamine, triethanolamine, 2-amino-2-methylpropanol, aminomercaptopropanediol, triisopropanolamine, glycine, histidine, alginine and the like. These salts may be prepared in a separate system and incorporated in a hair rinse composition. Alternatively, oxidation decomposition products or reduction derivatives of keratin material and alkaline materials may separately be added to a hair rinse composition in which they are converted to salts thereof. In the latter case, useful alkaline materials include, for example, sodium hydroxide, potassium hydroxide, aqueous ammonia, ethanolamine, diethanolamine, triethanolamine, 2-amino-2-methylpropanol, amino-methylmercaptopropanediol, triisopropanolamine, glycine, alginine, histidine and the like. Preferably, these alkaline materials are added in an amount of 0.1-8 equivalents of the carboxyl and sulfonic acid groups in the oxidation decomposition product or reduction derivative of keratin material.

The hair rinse composition according to the invention can be prepared by dissolving or dispersing 0.01-10 wt% (hereinafter referred to simply as %), preferably 0.1-5%, of one or more of decomposition derivatives of keratin material in a suitable solvent or liquid medium such as water, ethanol, glycerine, ethylene glycol, propylene glycol, 1, 3-propanediol, isopropanol, polyethylene glycol or the like.

Less amounts than 0.01% of decomposition derivatives of keratin material are unfavorable since a satisfactory effect cannot be produced, whereas larger amounts than 10% are not favorable since hair undesirably becomes sticky under high humidity doncitions.

To the hair rinse composition according to the present invention may be added, aside from the essential component of keratin decomposition derivatives, known ingredients which are employed in ordinary hair rinses. It is preferable to incorporate a surface active agent selected from anionic surface active agents, nonionic surface active agents and amphoteric surface active agents as an auxiliary component.

Examples of these surface active agents are as follows.

(1) Anionic Surface Active Agents

* Linear or branched alkylbenzenesulfonates having an alkyl group having 10–16 carbon atoms on average.
* Alkyl or alkenyl methoxysulfates having a linear or branched alkyl or alkenyl group having 8–20 carbon atoms on average and having ethylene oxide added in an amount of 0.5–8 moles per molecule on average.
* Alkyl or alkenylsulfates having an alkyl or alkenyl group having 10–20 carbon atoms on average.
* Olefinsulfonates having 10–20 carbon atoms in one molecule on average.
* Alkanesulfonates having 10–20 carbon atoms in one molecule on average.
* Saturated or unsaturated fatty acid salts having 10–20 carbon atoms in one molecule on average.
* Alkyl or alkenyl ethoxycarbonates having an alkyl or alkenyl group having 10–20 (preferably 12–16) carbon atoms on average and having 0.5–8 moles of ethylene oxide added in one molecule on average.
* α-sulfofatty acid salts or esters of the following formula

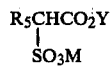

(in which Y represents an alkyl group having 1–3 carbon atoms or a counter ion, M is a counter ion, and $R_5$ represents an alkyl or alkenyl group having 10–20 (preferably 12–16) carbon atoms).

The counter ions of the anionic surface active agent include alkali metal ions such as sodium, potassium and the like, alkaline earth metal ions such as calcium, magnesium and the like, ammonium ion, ions of alkanolamines 1–3 alkanol groups having 2–3 carbon atoms (such as, for example, monoethanolamine, diethanolamine, triethanolamine, triisopropanolamine and the like).

(2) Nonionic Surface Active Agents

* Polyoxyethylene alkyl or alkenyl ethers having a primary or secondary alkyl or alkenyl group having 8–20 carbon atoms on average and having 3–12 moles of ethylene oxide added thereto.
* Polyoxyethylene alkylphenyl ethers having an alkyl group having 8–12 carbon atoms on average and having 3–12 moles of ethylene oxide added thereto.
* Higher fatty acid alkanolamides of the following formula or their alkylene oxide adducts

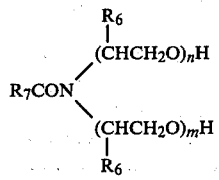

(in which $R_6$ represents H or $CH_3$, $R_7$ represents an alkyl or alkenyl group having 10–20 carbon atoms, n is an integer of 1–3, and m is an integer of 0–3).

(3) Amphoteric Surface Active Agents a. Alkylamine oxides of the following formulas

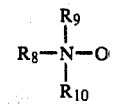

(in which $R_8$ represents an alkyl or alkenyl group having 10–20 carbon atoms, and $R_9$ and $R_{10}$ are independently an alkyl group having 1–3 carbon atoms).

It is preferable that, in the above formula, $R_8$ is the group having 12–16 carbon atoms and both $R_9$ and $R_{10}$ are each a methyl group.

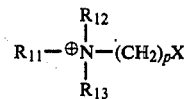

(in which $R_{11}$ represents an alkyl or alkenyl group having 10–20 carbon atoms, $R_{12}$ and $R_{13}$ independently represent an alkyl group having 1–4 carbon atoms, p is an integer of 1–3, and X represents a —COO⁻ or —SO₃⁻ group).

Preferably, in the above formula, $R_{11}$ is the group having 12–16 carbon atoms, $R_{12}$ and $R_{13}$ independently a methyl group, and p is a value of 3.

c. Imidazoline compounds of the following formula

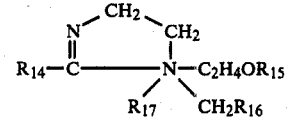

(in which $R_{14}$ represents a fatty acid residue having 10–20 carbon atoms on average, $R_{15}$ represents hydrogen, Na, or CH₂COOMe (Me: H, Na, or an organic base), $R_{16}$ represents COOMe,

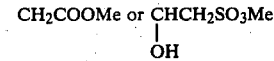

(Me has the same meaning as defined above), and $R_{17}$ represents a hydroxyl group, an acidic salt, or an anionic surface active sulfate or sulfatized product).

Preferably, in the above formula, $R_{14}$ represents a fatty acid residue having 12–16 carbon atoms.

Among these surface active agents, the anionic surface active agents and particularly alkyl ethoxysulfates having a linear or branched alkyl group having 12–16 carbon atoms and having 1–4 moles of ethylene oxide added in one molecule thereof or linear or branched alkylsulfates having 12–16 carbon atoms on average are preferable.

Good results are obtained when these surface active agents are added in an amount of 0.01–5%, preferably 1–2%, based on the hair rinse composition.

Moreover, there may be added to the hair rinse composition of the invention a variety of ingredients which include: oils including hydrocarbons such as liquid paraffin, vaseline, solid paraffin and the like, esters such as isopropylmyristate, lanolin derivatives such as lanolin, refined lanolin, lanolin fatty acids, and the like, silicone derivatives such as dimethylpolysiloxane, methylphenylpolysiloxane, organo-modified polysiloxanes and the like, and polyethylene glycol, polypropylene glycol or its polymer, polyoxyalkylene alkyl ethers, polyoxyalkylene alkyl ether phosphates, and the like; polymeric materials such as hydroxyethyl cellulose, hydroxypropylmethyl cellulose, hydroxpropyl cellulose, methyl cellulose, cationized cellulose, cationized polymers and the like; and germicides, preservatives, perfumes, dyes and the like.

The present invention is particularly described by way of references and examples.

Reference 1

Preparation of decomposition derivatives by oxidation of keratin materials:

(a) Ten grams of wool fibers were immersed in 700 g of a 8% aqueous peracetic acid solution at room temperature for 1 day to effect the oxidation reaction. The resulting oxidized wool fibers were filtered, washed with water and immersed in 700 g of a 0.1N ammoniacal solution at room temperature for 1 day, permitting about 90% of the wool fibers to dissolve in the ammoniacal solution. About 1 g of insoluble matters were removed by filtration and the ammoniacal solution of keratose to be an oxidized decomposition product of wool keratin was admixed with 2N hydrochloric acid to adjust its pH to 4.0, whereupon α-keratose was settled as precipitate. This precipitate was filtered, washed with acetone and dried to obtain 5.4 g of α-keratose.

(b) Wool fibers were heated under pressure in an autoclave by the use of saturated steam of 6 kg/cm$^2$ for 6 minutes and were abruptly released into the air to obtain a porous puffed product. Ten grams of the puffed product which had been reduced to pieces, 250 g of formic acid, and 50 g of a 30% aqueous hydrogen peroxide solution were charged into a 500 ml three neck flask to immerse the pieces at room temperature for 1 day, whereupon no powder was found in the solution but foam-like masses were floated in the upper layer. This reaction mixture was filtered and the filtrates was poured into 1.5 liters of water, followed by adding hydrochloric acid to adjust the pH to 4. The resulting precipitate was collected by filtration and washed with 500 ml of water to obtain 4.5 g of α-keratose. To the insoluble matter from which the reaction product had been removed were added 350 ml of water and then an ammoniacal solution to adjust the pH to 11, and the matter was immersed at room temperature for 1 day. The system was filtered and hydrochloric acid was added to the filtrate to adjust the pH to 4. The resulting precipitate was collected by filtration to obtain 0.7 g of α-keratose. 1.4 g of the insoluble matters were found to be primarily made of β-keratose.

Reference 2

Preparation of decomposition derivatives by reduction of keratin materials:

(a) Ten grams of wool fibers were immersed in 600 ml of an aqueous solution with concentrations of 8M urea and 0.01M Tris buffer, to which was added 6 ml of 2-mercaptoethanol, followed by adjusting the pH to 10 by means of a 5N potassium hydroxide aqueous solution to conduct the reduction reaction in a stream of nitrogen at room temperature. About 3 hours after commencement of the reaction, the wool dissolved in the reaction solution in an amount of about 85% thereof. While controlling the pH of the system to not lower than 7 by the use of an aqueous 5N potassium hydroxide solution, 16.5 g of iodoacetic acid was gradually added and the pH of the system was finally adjusted to 8.5 to carry out the carboxmethylation reaction at room temperature for 2 hours. The reaction solution was filtered to remove insoluble matters from the solution and the resultant filtrate was charged into a cellulose tube wherein it was dialyzed against ion-exchanged water to remove low molecular weight impurities including urea. As the urea was dialyzed, the content in the cellulose tube became cloudy since HGT (component with high contents of gylcine and tyrosine) to be a water-insoluble matter precipitated. After completion of the dialysis, the HGT was removed by centrifugal separation and S-carboxymethyl keratin (SCMKA) was obtained from the neutral transparent aqueous solution of SCMKA by the isoelectric precipitation method. That is, 1N hydrochloric acid was added to the system to adjust its pH to 4.4 by which SCKMA became insoluble and separated as precipitate. This precipitate was filtered, washed with ethanol and dried to obtain 4.2 g of SCMKA.

(b) The procedure of Reference 2(a) was repeated except that there was used instead of wool fibers feathers which were heated for 6 minutes in an autoclave by means of superheated steam of 6 kg/cm$^2$ and 240° C. and then abruptly released into the air to obtain a porous puffed product and that 1.75 g of maleic acid was used instead of iodoacetic acid, thereby obtaining 5.3 g of S-(1,2-dicarboxyethyl)-keratin.

(c) The procedure of Reference 2(a) was repeated using a powder of hoof of horse instead of wool fibers and 11 g of acrylic acid instead of iodoacetic acid, thereby obtaining 4.2 g of S-(2-carboxyethyl)-keratin.

(d) The procedure of Reference 2(a) was repeated using 28 g of styrenesulfonic acid instead of iodoacetic acid, thereby obtaining 4.2 g of S-(2-carboxyethyl)-keratin.

(e) Eight grams of wool fibers were dispersed in 300 ml of n-propanol and 300 ml of a 0.1N Tris buffer solution. After substitution with nitrogen, 3.2 ml of tri-n-butylphosphine was added, followed by agitating at room temperature for 24 hours. The solution was filtered and to the resulting insoluble matters were added 400 ml of water, 9.28 g of maleic acid and about 30 ml of 5N potassium hydroxide to adjust the pH 8.0, followed by agitating at room temperature for 6 hours. To the reaction system was added about 20 ml of aqueous ammonia to adjust the pH to 11.5, after which it was agitated for 18 hours at room temperature. The reaction solution was filtered to remove insoluble matters therefrom and the resulting filtrate was placed in a cellulose tube in which it was dialyzed against ion-exchanged water to remove low molecular weight impurities. After completion of the dialysis, the insoluble matters in the cellulose tube were removed by centrifugal separation and the resulting neutral transparent aqueous solution was adjusted to have a pH of 4.4 by addition of about 5.5 ml of 1N hydrochloric acid and the resulting precipitate was collected by filtration, followed by washing with ethanol and drying to obtain 3.9 g of S-(1, 2-dicarboxyethyl)-keratin.

(f) The procedure of Reference 2(e) was repeated except that there was used instead of wool fibers a powder of a porous puffed product of wool which was obtained by heating wool in an autoclave by means of saturated steam of 6 kg/cm$^2$ for 6 minutes and that 16.5 g of 2-acrylamido-2-methylpropanesulfonic acid was used instead of maleic acid, thereby obtaining 4.5 g keratin-S-(2-acrylamido-2-methylpropanesulfonic acid).

EXAMPLE 1

Hairs with a weight of 10 g and a length of 10 cm were treated with each hair rinses of the following compositions and completely dried by a dryer to compare ito softness, gloss and resilience (tensity and firmness of hair) with non-treated hairs. The comparison was made by a female expert panel of ten members according to the following evaluation standard. Table 1 shows average values of the evaluation.

Evaluation Standard:

| Evaluation Point | Softness As compared with non-treated hair | Gloss As compared with non-treated hair | Resilience As compared with non-treated hair |
|---|---|---|---|
| 5 | much better | much better | much better |
| 4 | better | better | better |
| 3 | equal | equal | equal |
| 2 | slightly poorer | slightly poorer | slightly poorer |
| 1 | poorer | poorer | poorer |

TABLE 1

Results

| | Decomposition Derivative of Keratin | Surface Active Agent or Oil | Softness | Gloss | Resilience |
|---|---|---|---|---|---|
| 1 | — | — | 3.0 | 3.0 | 3.0 |
| 2 | — | cetyltrimethyl-ammonium chloride | 4.0 | 3.5 | 0.5 |
| 3 | — | purified lanolin | 3.6 | 3.5 | 1.8 |
| 4 | — | N—laurylbetaine | 2.5 | 3.0 | 3.1 |
| 5 | — | | 2.7 | 3.1 | 3.3 |
| 6 | — | myristylamine oxide | 2.5 | 3.0 | 2.1 |
| 7 | — | ammonium laurylsulfate | 3.5 | 3.5 | 2.9 |
| 8 | — | polyoxyethylene nonyl-phenyl-ether | 3.3 | 3.1 | 2.5 |
| 9 | product of reference 1(a) | — | 3.9 | 4.2 | 4.5 |
| 10 | product of reference 1(b) | — | 3.7 | 4.1 | 4.2 |
| 11 | product of reference 2(a) | — | 4.0 | 3.9 | 4.0 |
| 12 | product of reference 2(c) | — | 3.9 | 4.2 | 3.9 |
| 13 | product of reference 1(a) | N—laurylbetaine | 4.0 | 3.9 | 4.2 |
| 14 | product of reference 1(a) | laurylimidazoline | 4.1 | 3.8 | 4.3 |
| 15 | product of reference 1(a) | myristylamine oxide | 4.0 | 4.0 | 3.9 |
| 16 | product of reference 1(a) | ammonium laurylsulfate | 4.2 | 4.5 | 3.6 |
| 17 | product of reference 1(a) | polyoxyethylene nonylphenyl ether | 4.0 | 3.6 | 4.0 |
| 18 | product of reference 1(a) | purified lanolin | 4.8 | 4.5 | 4.4 |
| 19 | product of reference 2(a) | N—laurylbetaine | 4.5 | 3.5 | 4.0 |
| 20 | product of reference 2(a) | laurylimidazoline | 4.1 | 3.9 | 3.8 |
| 21 | product of reference 2(a) | myristylamine oxide | 3.8 | 4.1 | 3.9 |
| 22 | product of reference 2(a) | ammonium laurylsulfate | 4.2 | 4.2 | 4.0 |
| 23 | product of reference 2(a) | polyoxyethylene nonylphenyl ether | 4.0 | 3.7 | 3.7 |
| 24 | product of reference 2(a) | purified lanolin | 4.6 | 3.6 | 3.9 |

| Formulation: | |
|---|---|
| Decomposition derivative of keratin (in the case of compositions of invention) | 1.0(%) |
| Surface active agent or oil | 1.0 |
| Water | balance |
| Caustic soda | suitable amount (pH 7.0) |

EXAMPLE 2

| Transparent Hair Rinse: | |
|---|---|
| a. Decomposition product obtained by oxidation of keratin (Reference 1(a)) | 1.0(%) |
| b. N—laurylbetaine | 3.0 |
| c. Ethanol | 10.0 |
| d. Polyoxyethylene (20) lauryl ether | 2.0 |
| e. Methyl cellulose | 0.5 |
| f. Water | balance | a and e were dispersed and dissolved in f, to which was added a mixture of b, d and d to obtain the present composition. Hair which had been treated with this composition were excellent in softness, gloss and resilience.

EXAMPLE 3

| | Creamy Hair Rinse: | |
|---|---|---|
| a. | Reduction derivative of keratin (Reference 2(a)) | 2.0(%) |
| b. | Cetyl alcohol | 2.0 |
| c. | Laurylamine oxide | 1.0 |
| d. | Ammonium laurylsulfate | 1.0 |
| e. | Polyoxyethylene (40) hardened castor oil | 0.5 |
| f. | Propylene glycol | 7.0 |
| g. | Hydroxyethyl cellulose | 0.5 |
| h. | Water | balance | a and g were dispersed and dissolved in h and heated to 60° C. To the solution was added a mixture of b-f, followed by cooling to room temperature to obtain the present composition. Hair treated with this composition was excellent in softness, gloss and resilience.

What is claimed is:

1. A hair rinse composition comprising, in liquid medium, 0.1-10 wt% of at least one decomposition derivative of keratin material selected from the group consisting of (1) salts of decomposition products obtained by oxidation of keratin material to convert the disulfide bonds to sulfonic acid groups, and (2) salts of derivatives at thiol groups of decomposition products obtained by reduction of keratin material, wherein the derivative at the thiol groups is a member selected from the group consisting of $-SCH_2COOH$,

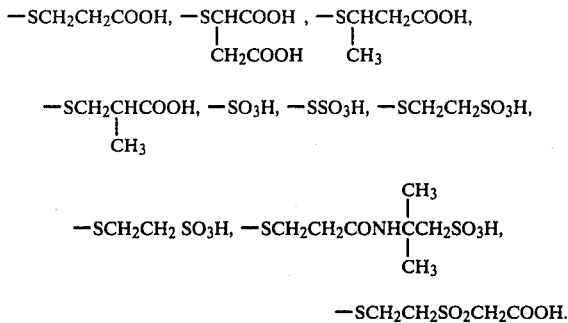

2. A hair rinse composition according to claim 1, wherein said at least one decomposition derivative is contained in an amount of 0.1-5 wt% of the composition.

3. A hair rinse composition according to claim 1, further comprising 0.01-5 wt% of at least one surface active agent selected from the group consisting of anionic surface active agents, nonionic surface active agents and amphoteric surface active agents.

4. A hair rinse composition according to claim 5, wherein said at least one surface active agent is contained in an amount of 1-2 wt% of the composition.

5. A hair rinse composition according to claim 5 or 6, wherein said at least one surface active agent is an alkyl ethoxysulfate having a linear or branched alkyl group having 12-16 carbon atoms and having 1-4 moles of ethylene oxide in one molecule thereof or a linear or branched alkylsulfate having 12-16 carbon atoms on average.

* * * * *